United States Patent
Silva Guisasola et al.

(10) Patent No.: US 9,000,195 B2
(45) Date of Patent: Apr. 7, 2015

(54) PROCESS FOR OBTAINING OLOPATADINE AND INTERMEDIATES

(75) Inventors: Luis Octavio Silva Guisasola, Boecillo-Valladolid (ES); Lydia Mateos Burón, Boecillo-Valladolid (ES); Antonio Lorente Bonde-Larsen, Boecillo-Valladolid (ES); Luis Gerardo Gutiérrez Fuentes, Boecillo-Valladolid (ES)

(73) Assignee: Crystal Pharma, S.A.U., Boecillo-Valladolid (ES)

( * ) Notice: Subject to any disclaimer, the term of this patent is extended or adjusted under 35 U.S.C. 154(b) by 526 days.

(21) Appl. No.: 13/054,210

(22) PCT Filed: Jul. 14, 2009

(86) PCT No.: PCT/EP2009/058974
§ 371 (c)(1),
(2), (4) Date: Apr. 6, 2011

(87) PCT Pub. No.: WO2010/007056
PCT Pub. Date: Jan. 21, 2010

(65) Prior Publication Data
US 2012/0004426 A1    Jan. 5, 2012

(30) Foreign Application Priority Data
Jul. 16, 2008 (EP) .................... 08380218

(51) Int. Cl.
*C07D 313/12* (2006.01)
(52) U.S. Cl.
CPC .................... *C07D 313/12* (2013.01)
(58) Field of Classification Search
None
See application file for complete search history.

(56) References Cited

U.S. PATENT DOCUMENTS

| | | | |
|---|---|---|---|
| 4,585,788 A | 4/1986 | Helsley et al. | |
| 4,871,865 A | 10/1989 | Lever, Jr. et al. | |
| 5,116,863 A * | 5/1992 | Oshima et al. | 514/450 |
| 2007/0232814 A1 | 10/2007 | Bader et al. | |

FOREIGN PATENT DOCUMENTS

| | | |
|---|---|---|
| EP | 214779 A1 | 3/1987 |
| EP | 235796 A2 | 9/1987 |
| WO | 2006010459 A1 | 2/2006 |
| WO | WO2009081417 * | 11/2008 |
| WO | 2009081417 A2 | 7/2009 |

OTHER PUBLICATIONS

Xue et al., Chinese Journal of Medicinal Chemistry, vol. 14, No. 6, p. 363-367.*
Oshima et al., J. Med. Chem. 1992, 35, 2074-2084.*
J. Prous, et al.; "KW-4679," Drugs of the Future, 1993, pp. 794-798, vol. 18.
EPO Communication Pursuant to Rule 114(2) EPC, Oct. 2, 2012.
Ohshima E., et al., Synthesis and Antiallergic Activity of 11-(Aminoalkylidene)-6,11-dihydrodibenz[b,e]oxepin Derivatives, J. Med. Chem., 1992, pp. 2074-2084, vol. 35.

* cited by examiner

Primary Examiner — Sun Jae Yoo
(74) Attorney, Agent, or Firm — Tristan A. Fulerer; Moore & Van Allen, PLLC

(57) ABSTRACT

Olopatadine can be obtained by means of a process comprising hydrolysis of a compound of general formula (II), wherein Y is $OR_1$, wherein $R_1$ is $C_1$-$C_7$ alkyl, $C_3$-$C_7$ cycloalkyl, aryl, arylalkyl, or heterocycle; or $NR_2R_3$, wherein $R_2$ and $R_3$, independently from each other, are $C_1$-$C_7$ alkyl, aryl, arylalkyl, or $R_2$ and $R_3$ together with the nitrogen atom to which they are bound form a heterocycle of 3 to 7 members, obtained by means of a process comprising reacting the corresponding ester or amide of 6,11-dihydro-11-oxodibenz[b,e]oxepin-2-acetic acid with a suitable Wittig reagent, in the presence of a base in a reaction medium comprising an organic solvent.

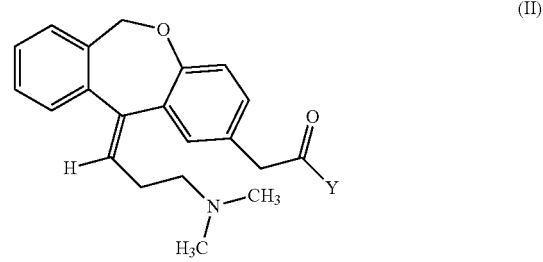

(II)

18 Claims, No Drawings

PROCESS FOR OBTAINING OLOPATADINE AND INTERMEDIATES

CROSS-REFERENCE TO RELATED APPLICATIONS

This application is filed under the provisions of 35 U.S.C. §371 and claims the priority of International Patent Application No. PCT/EP2009/058974 filed on 14 Jul. 2009 entitled "Process for Obtaining Olopatadine and Intermediates" in the name of Luis Octavio SILVA GUISASOLA, et al., which claims priority of European Patent Application No. EP08380218.1 filed on 16 Jul. 2008, both of which are hereby incorporated by reference herein in their entirety.

FIELD OF THE INVENTION

The invention relates to a process for obtaining esters and amides of Olopatadine useful for the production of Olopatadine and salts thereof. The invention also relates to some intermediates useful for producing Olopatadine and salts thereof.

BACKGROUND OF THE INVENTION

Olopatadine hydrochloride [(Z)-11-(3-dimethylaminopropylidene)-6,11-dihydrodibenz[b,e]oxepin-2-acetic acid hydrochloride], of formula

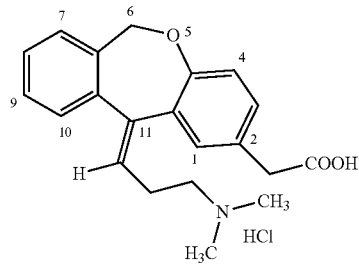

is a selective antagonist of H1 receptors of histamine, which is used in the treatment of ocular symptoms typical of seasonal allergic conjunctivitis. It is also used in the symptomatic treatment of allergic rhinitis and of urticaria as well as in the treatment of eczema and dermatitis. Olopatadine hydrochloride can be administered in a solid oral pharmaceutical dosage form or as an ophthalmic solution.

Olopatadine and pharmaceutically acceptable salts thereof are described in patents EP 214779, U.S. Pat. No. 4,871,865, EP 235796 and U.S. Pat. No. 5,116,863. Patent EP 214779 describes two general processes for the production of Olopatadine, one of them involving a Wittig reaction and the other a Grignard reaction followed by a dehydration step.

U.S. Pat. No. 5,116,863 describes the production of Olopatadine hydrochloride by several different processes, two of which include a Grignard reaction for introducing the side chain in position 11 and a third process (called "Process C" in said patent) in which said side chain is introduced in position 11 by means of a Wittig reaction. In a specific embodiment (Example 9), the Wittig reaction is performed on the 6,11-dihydro-1'-oxodibenz[b,e]oxepin-2-acetic acid (3) substrate, also known as Isoxepac, which is reacted with (3-dimethylaminopropyl)-triphenylphosphonium bromide hydrobromide, in the presence of n-butyl lithium giving rise to a Z/E mixture of Olopatadine together with salts of phosphorus which, after purifying by means of transforming it into the methyl ester of Olopatadine (2) and subsequent hydrolysis, provides Olopatadine hydrochloride (1), as shown in reaction scheme 1.

Reaction scheme 1

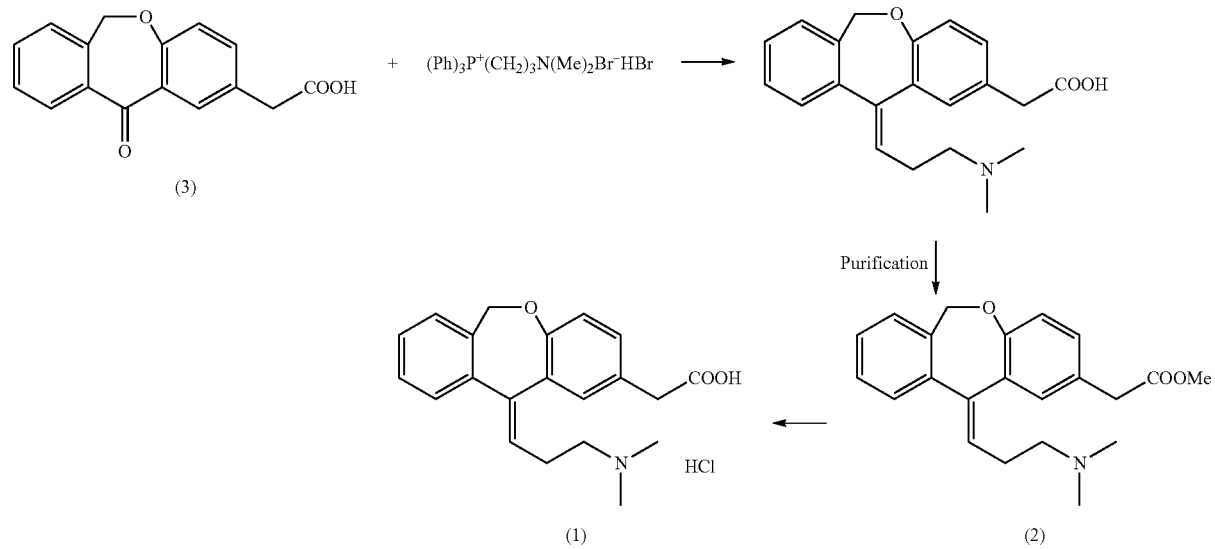

In the process shown in reaction scheme 1, the Wittig reagent [(Ph)₃P⁺(CH₂)₃N(Me)₂Br⁻HBr] is used in excess of up to 5 equivalents per equivalent of Isoxepac (3), a dangerous reagent (n-butyl lithium) is used; the process is very long and includes a number of extractions, changes of pH, in addition to esterification and subsequent saponification, the process therefore having very low yields and being rather expensive. The Z/E isomer ratio obtained in said process is not described.

Ohshima E., et al., in *J. Med. Chem.*, 1992, 35:2074-2084 (designated inventors in U.S. Pat. No. 5,116,863) describe several methods for synthesizing Olopatadine hydrochloride and other compounds of similar structure by means of Grignard reactions in some cases, and by means of Wittig reactions in other cases, for introducing the side chain (3-dimethylaminopropylidene). Following the synthetic scheme shown in reaction scheme 1, they start from type (3) compounds with free carboxylic acid and use (i) as base, n-butyl lithium, in a ratio relative to the type (3) compound of 7.5 equivalents of base/equivalent of type (3) compound and (ii) as Wittig reagent, (3-dimethylaminopropyl)-triphenylphosphonium bromide hydrobromide, in a ratio relative to the type (3) compound of 4.9 equivalents of the Wittig reagent/equivalent of type (3) compound. Once the Wittig reaction is carried out, in order to be able to better isolate the products, the acid is subsequently esterified; thus, and after purification by means of column chromatography, the obtained Z/E isomer ratio is 2:1. In said article, the authors (page 2077) acknowledge that when they try to perform this same Wittig reaction starting from a type (3) compound having an ester group instead of a carboxylic acid, the reaction does not occur and the starting material is recovered without reacting. This process has several drawbacks since it needs large amounts both of the Wittig reagent and of the base, n-butyl lithium (dangerous reagent, as already mentioned), it needs esterification, column purification, saponification and purification again, whereby the global process is not efficient.

Application WO 2006/010459 describes obtaining Olopatadine hydrochloride by means of a process in which a Wittig reaction is also performed but, this time, on an open substrate with final cyclization to form oxepin by means of Pd catalyst as can be seen in reaction scheme 2.

The process shown in reaction scheme 2 has several drawbacks: high number of synthesis steps, the use of palladium catalysts which increase the cost of the process, the obtained Z/E isomer ratio is only 2.5:1 in favor of the Z isomer, and, finally, the need of using ionic exchange resins and chromatography columns, together with the use of dangerous reagents such as lithium aluminium hydride, n-butyl lithium or Jones reagent, make the process unfeasible on an industrial scale.

Application US2007/0232814 describes obtaining Olopatadine hydrochloride by means of a process which includes a Wittig reaction between Isoxepac (3) and the corresponding Wittig reagent [(3-dimethylaminopropyl)-triphenylphosphonium halides or salts thereof], using as base sodium hydride (NaH), whereby obtaining Olopatadine base which, after subsequent formation of an addition salt (essential for the production and isolation of the product of interest) and purification, yields Olopatadine hydrochloride (1), as shown in reaction scheme 3.

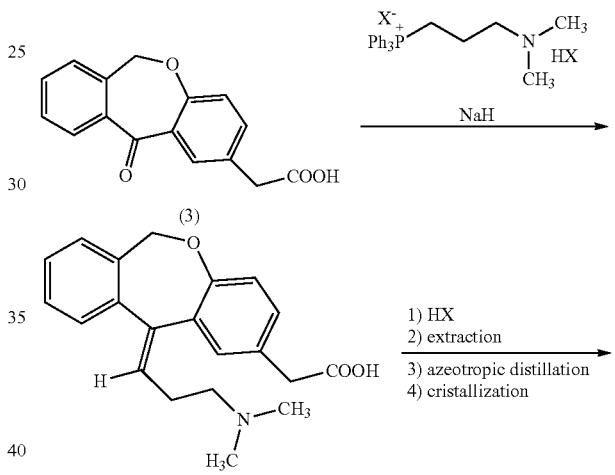

Reaction scheme 3

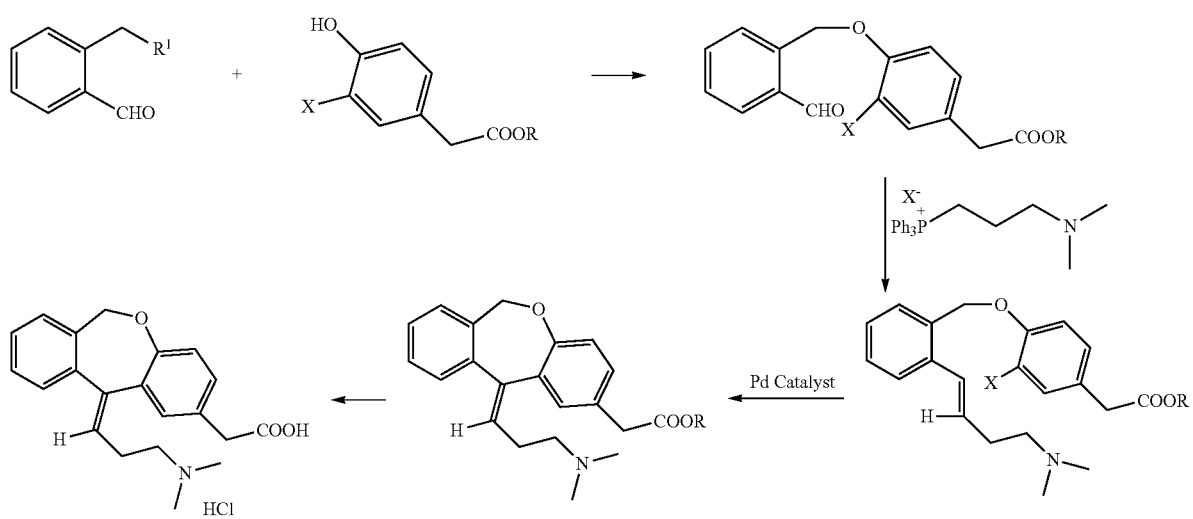

Reaction scheme 2

[R is an acid protecting group, especially C₁-C₄ alkyl]

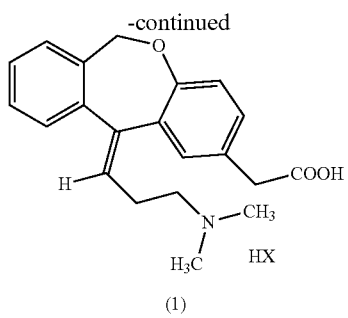

(1)

[X = Cl]

In the process shown in scheme 3, the amounts of Wittig reagent and of base used are very high since when the Wittig reagent is used in the form of salt 2.7 equivalents and 8.1 equivalents of base (NaH) are used, whereas if the free Wittig reagent is used 2.7 equivalents and 4.0 equivalents of base (NaH) are used. In these conditions, the reaction is very long (it can last more than one day) and the obtained Z/E isomer ratio is only 2.3:1, which results in a relatively low final yield and makes subsequent purification necessary. This process is, in addition, slow and tedious, therefore it is not very attractive from the industrial point of view.

It is therefore necessary to develop an alternative process for obtaining Olopatadine hydrochloride which overcomes all or part of the problems associated to the processes known in the state of the art.

SUMMARY OF THE INVENTION

The invention takes on the problem of providing an alternative process for obtaining Olopatadine and salts thereof, which overcomes all or part of the problems existent in the different syntheses of Olopatadine and salts thereof, in particular, of the previously mentioned syntheses which involve performing a Wittig reaction in relation to the state of the art.

The solution provided by the invention is based on the fact that the inventors have observed that it is surprisingly possible to efficiently obtain (Z)-11-(3-dimethylaminopropylidene)-6,11-dihydrodibenz[b,e]oxepin-2-acetic acid (Olopatadine) and salts thereof by means of a process comprising performing a Wittig reaction between a Wittig reagent selected from a (3-dimethylaminopropyl)-triphenylphosphonium halide and salts thereof, with an ester or with a 6,11-dihydro-1'-oxodibenz[b,e]oxepin-2-acetic acid amide, in the presence of a base, an organic solvent and, optionally, an organic polar aprotic cosolvent, and, subsequently, subjecting the obtained compound (Olopatadine ester or amide) to a hydrolysis reaction of the protected carboxylic acid for obtaining the corresponding free acid (Olopatadine), and, if desired, converting said compound into a salt.

A process such as the one provided by the present invention has several advantages since the use of very dangerous reagents such as n-butyl lithium is not required, and the reagents are used in lower relative amounts than that previously described in the state of the art for this type of reactions, making a better isolation and a higher purity of the product of interest possible without having to use costly purification techniques (e.g., chromatography), making this process more advantageous from the industrial point of view. Furthermore, and surprisingly, high Z/E isomer ratios, up to 4/1 in some cases, are obtained, increasing the global yield of the reaction compared to the previously described processes, further enabling simpler isolation of the product of interest.

Additionally, it should be emphasized that the use of 6,11-dihydro-11-oxodibenz[b,e]oxepin-2-acetic acid esters in Wittig reactions, using as Wittig reagent a (3-dimethylaminopropyl)-triphenylphosphonium halide or a salt, for obtaining the corresponding condensation products, was clearly discarded by Ohshima et al. (*J. Med. Chem.*, 1992, 35:2074-2084), opposite to which is disclosed in the present invention.

Therefore in one aspect, the invention relates to a process for the production of an ester or amide of Olopatadine comprising subjecting an ester or an amide of 6,11-dihydro-11-oxodibenz[b,e]oxepin-2-acetic acid to a Wittig reaction using as Wittig reagent a (3-dimethylaminopropyl)-triphenylphosphonium halide or salts thereof, in the presence of a base, one or more organic solvents, and, optionally, an organic polar aprotic cosolvent.

In another aspect, the invention relates to a process for obtaining Olopatadine, solvates or salts thereof, comprising hydrolyzing said ester or amide of Olopatadine.

In another aspect, the invention relates to a process for obtaining (Z)-11-(3-dimethylaminopropylidene)-6,11-dihydrodibenz[b,e]oxepin-2-acetic acid isopropyl ester, comprising reacting a 6,11-dihydro-11-oxodibenz[b,e]oxepin-2-acetic acid with isopropyl alcohol in an acid reaction medium comprising an organic solvent and subsequently subjecting the obtained intermediate to a Wittig reaction using a (3-dimethyl-aminopropyl)-triphenylphosphonium halide or a salt thereof, in the presence of a base, in a reaction medium comprising an organic solvent, and, optionally, an organic polar aprotic cosolvent.

In another aspect, the invention relates to a compound selected from 6,11-dihydro-11-oxodibenz[b,e]oxepin-2-acetic acid dimethylamide, (Z)-11-(3-dimethylaminopropylidene)-6,11-dihydrodibenz[b,e]oxepin-2-acetic acid isopropyl ester and (Z)-11-(3-dimethylaminopropylidene)-6,11-dihydrodibenz[b,e]oxepin-2-acetic acid benzyl ester. Said compounds are useful intermediates in the synthesis of Olopatadine.

DETAILED DESCRIPTION OF THE INVENTION

In one aspect, the invention relates to a process, hereinafter process of the invention, for obtaining a compound of general formula (II)

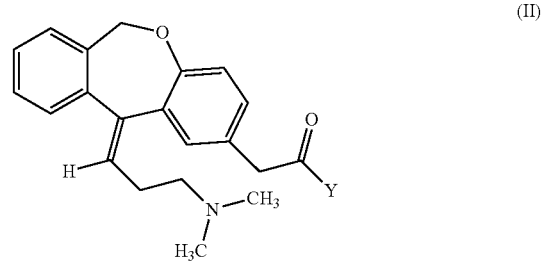

(II)

wherein

Y is

OR$_1$, wherein R$_1$ is C$_1$-C$_7$ alkyl, C$_3$-C$_7$ cycloalkyl, aryl, arylalkyl, or heterocycle; or NR$_2$R$_3$, wherein R$_2$ and R$_3$, independently from each other, are C$_1$-C$_7$ alkyl, aryl, arylalkyl, or R$_2$ and R$_3$ together with the nitrogen atom to which they are bound form a heterocycle of 3 to 7 members,
solvates or salts thereof,
comprising
a) reacting a compound of general formula (III)

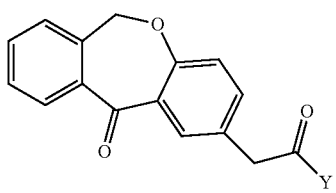

(III)

wherein Y has the previously mentioned meaning,
with a Wittig reagent selected from the group consisting of a (3-dimethylaminopropyl)-triphenylphosphonium halide and salts thereof, under Wittig reaction conditions, in the presence of a base in a reaction medium comprising an organic solvent, for obtaining a compound of general formula (II); and
b) if desired, converting the compound of general formula (II) into a solvate or into a salt thereof.

The term "$C_1$-$C_7$ alkyl", as used herein, relates to a radical derived from a linear or branched alkane of 1 to 7 carbon atoms, for example, methyl, ethyl, n-propyl, isopropyl, butyl, tertbutyl, etc., optionally substituted by one or more substituents independently selected from halogen, hydroxyl, $C_1$-$C_3$ haloalkyl, $C_1$-$C_3$ alkyl and $C_2$-$C_3$ alkenyl.

The term "$C_1$-$C_3$ alkyl", as used herein, relates to a radical derived from a linear or branched alkane of 1 to 3 carbon atoms, for example, methyl, ethyl, n-propyl, isopropyl, optionally substituted by one or more substituents independently selected from halogen, hydroxyl, $C_1$-$C_3$ haloalkyl, $C_1$-$C_3$ alkyl and $C_2$-$C_3$ alkenyl.

The term "$C_2$-$C_3$ alkenyl", as used herein, relates to a radical derived from an alkene of 2 or 3 carbon atoms, for example, ethenyl (vinyl), n-propenyl, isopropenyl, etc., optionally substituted by one or more substituents independently selected from halogen, hydroxyl, $C_1$-$C_3$ haloalkyl, $C_1$-$C_3$ alkyl and $C_2$-$C_3$ alkenyl.

The term "aryl", as used herein, relates to a radical derived from an aromatic hydrocarbon, optionally substituted by one or more substituents independently selected from halogen, $C_1$-$C_7$ alkyl, hydroxyl, $C_1$-$C_3$ haloalkyl and $C_2$-$C_3$ alkenyl, for example, phenyl, benzyl, tolyl, xylyl, etc., non-substituted or substituted by one or more of said substituents.

The term "arylalkyl", as used herein, relates to an alkyl group substituted with an aryl group, optionally substituted by one or more substituents independently selected from halogen, $C_1$-$C_7$ alkyl, hydroxyl, $C_1$-$C_3$ haloalkyl and $C_2$-$C_3$ alkenyl, for example, benzyl, etc., non-substituted or substituted by one or more of said substituents. Preferably, the term "arylalkyl" refers to a group having between 7 and 17 carbon atoms ("$C_7$-$C_{17}$ arylalkyl").

The term "$C_3$-$C_7$ cycloalkyl", as used herein, relates to a radical derived from a cycloalkane of 3 to 7 carbon atoms, for example, cyclopropyl, cyclobutyl, etc., optionally substituted by one or more substituents independently selected from halogen, hydroxyl, $C_1$-$C_3$ haloalkyl, $C_1$-$C_3$ alkyl and $C_2$-$C_3$ alkenyl.

The term "$C_1$-$C_3$ haloalkyl", as used herein, relates to a radical derived from a linear or branched alkane of 1 to 3 carbon atoms, wherein one or more hydrogens are substituted by halogen (e.g., fluorine, chlorine, bromine, etc.), for example, trifluoromethyl, trifluoroethyl, etc., optionally substituted by one or more substituents independently selected from hydroxyl, $C_1$-$C_3$ alkyl and $C_2$-$C_3$ alkenyl. Halogens present in the haloalkyl radical can be similar or different.

The term "heterocycle", as used herein, relates to a radical derived from a cyclic compound of 3 to 7 atoms which contains, being part of the cyclic structure, at least one atom different from carbon (heteroatom), e.g., oxygen, nitrogen, sulfur, etc., which can optionally be substituted by one or more substituents independently selected from halogen, $C_1$-$C_7$ alkyl, hydroxyl, $C_2$-$C_3$ alkenyl, for example, an azole, a pyridine, a furan, a pyrrole, an oxirane, an imidazole, a benzofuran, an indole, a pyrimidine, a thiazole, etc., non-substituted or substituted by one or more of said substituents.

A process such as the process of the invention has several advantages since, on one hand, (i) an amount of Wittig reagent and of base necessary to carry out the process of the invention that is substantially lower than that needed to carry out similar processes described in the state of the art is required due, among other reasons, to the fact that since the carboxyl group of the compound of formula (III) is protected (in the form of ester or amide), part of the phosphorus ylide generated by the action of the base on the Wittig reagent is not neutralized (by means of an acid-base reaction); as a result, since a lower amount of Wittig reagent and of base is required, the process of the invention is less expensive; and, moreover, (ii) since a lower amount of Wittig reagent is used, fewer salts and intermediates that are hard to remove from the process, such as triphenylphosphine oxide are generated, facilitating the subsequent treatment and isolation of the product of interest.

According to the process of the invention, the Wittig reaction is carried out between the compound of formula (III) and a Wittig reagent selected from the group consisting of a (3-dimethylaminopropyl)-triphenylphosphonium halide and salts thereof, under Wittig reaction conditions, in the presence of a base, in a reaction medium comprising an organic solvent. Said Wittig reagent, in the presence of a suitable base, e.g., a strong base, forms the intermediate reagent (phosphorus ylide) by means of the abstraction of a proton adjacent to the phosphorus atom, which attacks the carbonyl group of the compound of formula (III) until forming the compound of general formula (II), in turn obtaining the triphenylphosphine oxide which enhances the reaction as it is very stable.

The compound of general formula (III), used as a starting product in the process of the invention, is an ester or an amide of 6,11-dihydro-11-oxodibenz[b,e]oxepin-2-acetic acid (Isoxepac), and can be obtained by conventional methods known by the person skilled in the art, as described in several books or articles of reference, for example, "Protective groups in Organic Chemistry", Greene T. W., Wuts P. G. Wiley-Interscience, Third edition, 1999; "Advanced Organic Synthesis: Method and Techniques", Richard S. Monson, Academic Press, 1971; "Advanced Organic Chemistry", Francis A. Carey, Richard J. Sundberg, Kluwer Academic/Plenum Publishers, Fourth edition, 2000.

In a particular embodiment, the compound of general formula (III) is an ester [compound of formula (III) wherein Y is $OR_1$, wherein $R_1$ is $C_1$-$C_7$ alkyl, $C_3$-$C_7$ cycloalkyl, aryl, arylalkyl, or heterocycle], which can be obtained from Isoxepac by means of an esterification reaction, for example, by means of reaction with the suitable alcohol in an acid medium (Fischer esterification); by way of illustration, when Y is isopropyl, said isopropyl ester can be obtained by reacting Isoxepac with isopropanol in the presence of p-toluenesulfonic acid.

In another particular embodiment, the compound of general formula (III) is an amide [compound of formula (III) wherein Y is $NR_2R_3$, wherein $R_2$ and $R_3$, independently from each other, are $C_1$-$C_7$ alkyl, aryl, arylalkyl, or $R_2$ and $R_3$ together with the nitrogen atom to which they are bound form a heterocycle of 3 to 7 members], which can be obtained from Isoxepac after transformation in an acid chloride or in an ester, as previously described, and, subsequently, reacting it with an amine.

Particularly preferred compounds of formula (III) are those in which:
a) Y is $OR_1$, wherein $R_1$ is $C_1$-$C_7$ alkyl, preferably, ethyl or isopropyl; or, alternatively,
b) Y is $OR_1$, wherein $R_1$ is aryl or arylalkyl, preferably, benzyl; or, alternatively,
c) Y is $NR_2R_3$, wherein $R_2$ and $R_3$, independently from each other, are $C_1$-$C_7$ alkyl, aryl, arylalkyl, or together with the nitrogen atom to which they are bound form a heterocycle of 3 to 7 members, preferably, $R_2$ and $R_3$ are methyl.

Thus, in a particular and preferred embodiment, the compound of formula (III) is 6,11-dihydro-11-oxodibenz[b,e]oxepin-2-acetic acid dimethylamide of formula (IIIa)

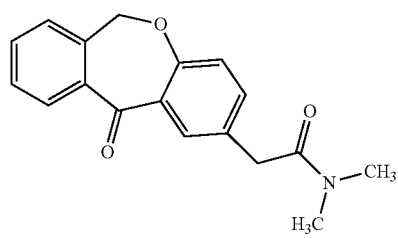

(IIIa)

Said amide of formula (IIIa) can be obtained in a particular embodiment from an ester, such as a compound of general formula (III) wherein Y is $OR_1$, wherein $R_1$ is $C_1$-$C_7$ alkyl, $C_3$-$C_7$ cycloalkyl, aryl, arylalkyl, or heterocycle, for example, 6,11-dihydro-11-oxodibenz[b,e]oxepin-2-acetic acid isopropyl ester of formula (IIIb)

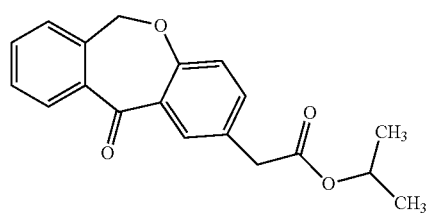

(IIIb)

by adding dimethylamine and heating in an organic solvent or in a mixture of several organic solvents; illustrative examples of said organic solvents include aromatic solvents (e.g., toluene, xylene, etc.).

Said amide of formula (IIIa) can be used as an intermediate in the synthesis of Olopatadine and salts thereof and constitutes an additional aspect of the present invention.

The Wittig reagent used to put the process of the invention into practice is selected from a (3-dimethylaminopropyl)-triphenylphosphonium halide and salts thereof.

In a particular embodiment, said Wittig reagent is a (3-dimethylaminopropyl)-triphenylphosphonium halide of general formula

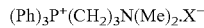

$(Ph)_3P^+(CH_2)_3N(Me)_2.X^-$ wherein Ph is phenyl and X is halogen, preferably, chlorine, bromine or iodine. In a specific embodiment, said (3-dimethylaminopropyl)-triphenylphosphonium halide is the (3-dimethylaminopropyl)-triphenylphosphonium bromide.

In another particular embodiment, said Wittig reagent is a salt of a (3-dimethylaminopropyl)-triphenylphosphonium halide of general formula

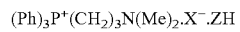

$(Ph)_3P^+(CH_2)_3N(Me)_2.X^-.ZH$ wherein Ph is phenyl and X and Z, independently from each other, represent a halogen, preferably, chlorine, bromine or iodine. In a specific embodiment, said salt of (3-dimethylaminopropyl)-triphenylphosphonium halide is (3-dimethylaminopropyl)-triphenylphosphonium bromide hydrobromide.

While the ratio (in equivalents) between the Wittig reagent and the compound of formula (III) can vary within a wide range, in a particular embodiment, the ratio between the Wittig reagent and the compound of formula (III) is comprised between 1 and 2 equivalents of Wittig reagent per equivalent of compound of formula (III).

The base used in the process of the invention can be almost any base capable of deprotonating the compound of formula (III), preferably, a base that is not very nucleophilic, for example, a metal hydride, a metal alkoxide, a metal amide, an amide with great steric volume, etc., and mixtures thereof. An "amide with great steric volume", as used herein, relates to an amide which has a marked base character and, due to its bulky size, is not very nucleophilic; therefore it does not have problems of undesired additions to the substrates. In a particular embodiment, said base is selected from the group consisting of an alkaline metal hydride, an alkaline-earth metal hydride, an alkaline metal alkoxide, an alkaline-earth metal alkoxide, an alkaline metal amide, an alkaline-earth metal amide, an amide with great steric volume, and mixtures thereof; illustrative, non-limiting examples of said bases include lithium hydride, sodium hydride, potassium hydride, calcium hydride, sodium ethoxide, potassium ethoxide, sodium tert-butoxide, potassium tert-butoxide, sodium bis(trimethylsilyl)amide, potassium bis(trimethylsilyl)amide and mixtures thereof, preferably, sodium hydride, potassium ethoxide, potassium tert-butoxide and mixtures thereof.

The ratio (in equivalents) between the base and the compound of formula (III) can vary within a wide range; nevertheless, in a particular embodiment, the ratio between the base and the compound of formula (III) is comprised between 1 and 2 equivalents of base per equivalent of compound of formula (III).

The Wittig reaction between the Wittig reagent and the compound of formula (III), in the presence of a base, is carried out in a reaction medium comprising a suitable organic solvent. In a particular embodiment, non-protic organic solvents are used, for example, aromatic solvents (e.g., toluene, xylene, etc.), halogenated solvents (e.g., methylene chloride, etc.), ethers, for example, aliphatic ethers (e.g., diisopropyl ether, di-tert-butyl ether, etc.), cyclic ethers (e.g., tetrahydrofuran (THF), methyl-tetrahydrofuran (MeTHF)), dioxane (e.g., 1,3-dioxane, 1,4-dioxane and derivatives thereof), etc., polar aprotic solvents (e.g., dimethylformamide (DMF), dimethylacetamide (DMA), etc.), and mixtures thereof. In a particular embodiment, said solvent is selected from an aromatic solvent (e.g., toluene, xylene, etc.), an aliphatic ether (e.g., diisopropyl ether, etc.), a cyclic ether (e.g., THF, dioxane, etc.), and mixtures thereof, preferably, THF, toluene and mixtures thereof.

The Wittig reaction between the Wittig reagent and the compound of formula (III) can be carried out at a temperature comprised between 0° C. and the reflux temperature of the solvent used, for a time period equal to or greater than 15 minutes, typically comprised between 30 minutes and 12 hours, usually between 3 and 6 hours.

In a particular embodiment, the Wittig reaction is carried out using a metal alkoxide (e.g., potassium ethoxide, potassium tert-butoxide, etc.) as a base in a reaction medium comprising THF as solvent.

In a preferred embodiment, the Wittig reaction is carried out using a metal alkoxide (e.g., potassium ethoxide, potassium tert-butoxide, etc.) as a base in a reaction medium comprising toluene as solvent.

It has additionally been observed that when the base is a metal hydride (e.g., sodium hydride (NaH)), the Wittig reaction surprisingly occurs very well when, in addition to the organic solvent, the medium comprises an organic polar aprotic cosolvent; while almost any organic polar aprotic solvent can be used as cosolvent in the process of the invention, in a particular embodiment, said organic polar aprotic cosolvent is selected from dimethylacetamide (DMA), dimethylformamide (DMF), N-methylpyrrolidone (NMP), N-methylmorpholine (NMM), and mixtures thereof, preferably, DMA, DMF and mixtures thereof, even more preferably, DMA.

The presence of said organic polar aprotic cosolvent favors (increases) the solubility of the base (e.g., sodium hydride or similar), normally insoluble in the reaction medium comprising THF or toluene as solvent, and therefore reacts much more quickly and efficiently forming the phosphorus ylide in short reaction times, which allows obtaining better yields.

The amount of said organic polar aprotic cosolvent eventually present in the reaction medium can vary within a wide range; nevertheless, in a particular embodiment, the amount of said organic polar aprotic cosolvent present in the reaction medium is comprised between 2% and 50% by volume, preferably, between 5% and 20% by volume of the cosolvent relative to the amount of solvent present in the reaction medium.

Several Isoxepac esters (e.g., ethyl, isopropyl, benzyl, etc.) have been tested, using a metal hydride (e.g., NaH) as a base and a reaction medium comprising, in addition to the organic solvent, an organic polar aprotic cosolvent (e.g., DMA), observing that the best results were obtained when the Isoxepac ester was the isopropyl ester. Therefore in a particular embodiment, the Wittig reaction is carried out using a compound of formula (III) wherein Y is $OR_1$, wherein $R_1$ is ethyl, isopropyl, or benzyl, preferably isopropyl, in the presence of NaH, in a reaction medium comprising DMA as organic polar aprotic cosolvent, preferably in a reaction medium comprising THF as organic solvent and DMA as organic polar aprotic cosolvent. In these conditions, the Wittig reaction occurs very well, with a high yield, using a very small amount of Wittig reagent, typically in the order of 1-1.6 equivalents of Wittig reagent per equivalent of compound of formula (III), which facilitates both the processing and the production of Olopatadine and salts thereof on an industrial level.

The process of the invention allows obtaining a Z/E isomer ratio higher than what would be expected according to the references of the state of the art. The Z/E isomer ratio can have some variation depending on the Y substituent present in the starting material [compound of formula (III)] for the Wittig reaction. In a particular embodiment, when the starting product is a compound of formula (III) wherein Y is $OR_1$, wherein $R_1$ is a $C_1$-$C_7$ alkyl group, the Z/E isomer ratio can be 3.5/1, or even higher, in favor of the desired Z isomer, i.e., higher than that obtained using Isoxepac (in which the typically obtained Z/E isomer ratio is 2.5/1). This Z/E isomer ratio was obtained using NaH as base and a reaction medium comprising THF as solvent and DMA as cosolvent. In a particular and preferred embodiment, the starting material is the isopropyl ester of Isoxepac [compound of formula (III) wherein Y is $OR_1$, wherein $R_1$ is isopropyl], which allows obtaining a Z/E isomer ratio in the order of 4/1.

The process of the invention allows obtaining compounds of general formula (II), solvates (including hydrates) and salts thereof.

Preferred compounds of general formula (II) are those in which:
a) Y is $OR_1$, wherein $R_1$ is $C_1$-$C_7$ alkyl, preferably, ethyl or isopropyl; or, alternatively,
b) Y is $OR_1$, wherein $R_1$ is aryl or arylalkyl, preferably, benzyl; or, alternatively,
c) Y is $NR_2R_3$, wherein $R_2$ and $R_3$, independently from each other, are $C_1$-$C_7$ alkyl, aryl, arylalkyl, or together with the nitrogen atom to which they are bound form a heterocycle of 3 to 7 members, preferably, $R_2$ and $R_3$ are methyl.

Particularly preferred compounds of general formula (II) include:

(Z)-11-(3-dimethylaminopropylidene)-6,11-dihydrodibenz[b,e]oxepin-2-acetic acid isopropyl ester of formula (IIa)

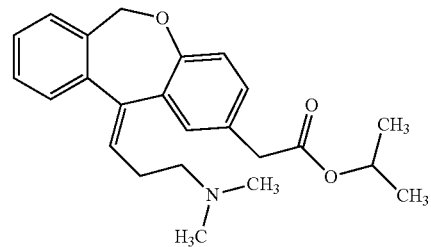

(IIa)

(Z)-11-(3-dimethylaminopropylidene)-6,11-dihydrodibenz[b,e]oxepin-2-acetic acid benzyl ester of formula (IIb)

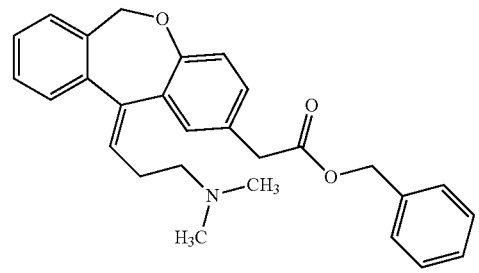

(IIb)

The esters of formulas (IIa) and (IIb) can be used as intermediates in the synthesis of Olopatadine and salts thereof and constitute additional aspects of the present invention.

The compound of general formula (II) is an amine and can form addition salts with organic or inorganic acids when reacting with a stoichiometric amount of the suitable acid in water, in an organic solvent or in a mixture of both. The preferred non-aqueous media are usually diisopropyl ether, ethyl acetate, ethanol, isopropanol or acetonitrile. Included among the acid addition salts are mineral acid addition salts such as hydrochloride, hydrobromide, sulfate, nitrate and phosphate, and organic acid addition salts such as acetate, maleate, fumarate, lactate, citrate, oxalate, succinate, tartrate, malate, mandelate, methanesulfonate and p-toluenesulfonate. Said salts can be obtained by conventional methods by reacting the free amine with the acid in question. In a particular embodiment, said salt is a pharmaceutically acceptable salt, for example, hydrochloride. Said salt can be obtained by reacting the free amine with hydrochloric acid. If desired, said addition salt can optionally be transformed into the corresponding free amine by conventional methods, for example, by varying the pH of a solution comprising said salt to obtain the free amine.

The compound of general formula (II) can be obtained in the form of free base or salt. In both cases it is preferably obtained in crystalline form, both as free compounds and solvates (for example, hydrates), both forms included within the scope of the present invention. The solvation methods are generally known in the state of the art.

The compounds of general formula (II) can be used for producing Olopatadine and salts thereof.

Therefore in another aspect, the invention relates to a process for obtaining Olopatadine of formula (I)

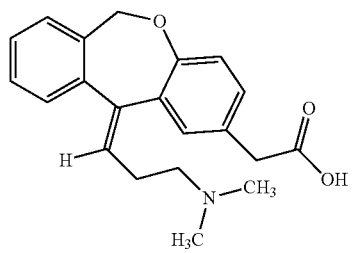

(I)

solvates and salts thereof,
comprising
a) reacting a compound of general formula (III)

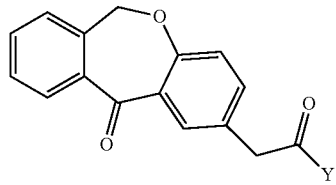

(III)

wherein Y is $OR_1$, wherein $R_1$ is $C_1$-$C_7$ alkyl, $C_3$-$C_7$ cycloalkyl, aryl, arylalkyl, or heterocycle; or $NR_2R_3$, wherein $R_2$ and $R_3$, independently from each other, are $C_1$-$C_7$ alkyl, aryl, arylalkyl or together with the nitrogen atom to which they are bound form a heterocycle of 3 to 7 members,
with a Wittig reagent selected from the group consisting of a (3-dimethylaminopropyl)-triphenylphosphonium halide and salts thereof, under Wittig reaction conditions, in the presence of a base in a reaction medium comprising an organic solvent, for obtaining a compound of general formula (II);

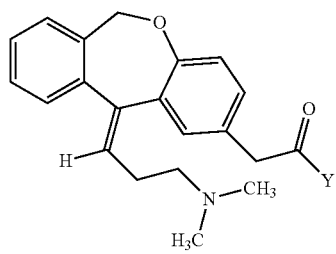

(II)

wherein Y has the previously mentioned meaning, and
b) if desired, converting the compound of general formula (II) into a solvate or into a salt thereof,
c) subjecting to hydrolisis the compound of general formula (II),
and, if desired,
d) converting said compound of formula (I) into a salt or solvate thereof.

The compound of general formula (II) can be obtained according to the reaction conditions mentioned above in relation with the previously described process of the invention. Hydrolysis of the ester or amide group present in the compound of general formula (II) to give the corresponding carboxylic acid can be performed by means of conventional methods, for example, any deprotection method generally described in chemistry books of reference such as "Protective groups in Organic Chemistry", Greene T. W., Wuts P. G. Wiley-Interscience, Third edition, 1999; "Comprehensive Organic Transformation", Richard C. Larock, VCH, Second edition, 1999.

Hydrolysis of the compound of general formula (II) can be base or acid.

In a particular embodiment, the compound of general formula (II) is subjected to a base hydrolysis by means of reaction with a base; non-limiting illustrative examples of bases that can be used include sodium hydroxide, potassium hydroxide, etc.

In another particular embodiment, the compound of general formula (II) is subjected to an acid hydrolysis by reacting with an acid, such as an organic (e.g., methanesulfonic acid, p-toluenesulfonic acid, etc.) or inorganic (e.g., hydrochloric acid, hydrobromic acid, sulfuric acid, nitric acid, phosphoric acid, etc.) acid and mixtures thereof.

In a particular and preferred embodiment, the acid hydrolysis is performed using hydrochloric acid since it allows the isolation of Olopatadine as hydrochloride, if desired.

Hydrolysis of the compound of general formula (II) is carried out in a reaction medium comprising an organic solvent, such as an alcohol (e.g., methanol, ethanol, isopropanol, etc.), a ketone (e.g., acetone, methyl ethyl ketone, etc.), a nitrile (e.g., acetonitrile, etc.), or mixtures thereof, or, alternatively, a mixture of said organic solvent and water, preferably, acetone, isopropanol or acetonitrile, optionally mixed with water. In a particular embodiment, said reaction medium comprises acetone, whereas in another particular embodiment, said reaction medium comprises acetone and water.

Hydrolysis of the compound of general formula (II), either until the deprotection is complete or until it reaches the equilibrium point, can be carried out within a wide range of temperatures; nevertheless, in a particular embodiment, said hydrolysis is carried out at a temperature comprised between room temperature (18-22° C.) and the reflux temperature of the solvent used, for a time period equal to or greater than 15 minutes, typically comprised between 30 minutes and 18 hours. In general, hydrolysis of the compound of general formula (II) can be accelerated by means of heating the reaction mixture. In a particular embodiment, this heating is performed at the reflux temperature of the acetone.

The compound of formula (I) [Olopatadine], which has the carboxylic acid deprotected, can be isolated by conventional methods, for example, the presence of an acid in the reaction mixture can give rise to the formation of the corresponding acid addition salt of the amine which precipitates in the form of a solid, which can be isolated by means of using conventional techniques known by the person skilled in the art. By way of illustration, if desired, the precipitation of the acid addition salt of Olopatadine can be caused, subjecting the compound of general formula (II) to acid hydrolysis in a reaction medium comprising one or more organic solvents, partially or totally miscible with water, for example, an alcohol (e.g., methanol, ethanol, isopropanol, etc.), a ketone (e.g., acetone, methyl ethyl ketone, etc.), a nitrile (e.g., acetonitrile, etc.), or mixtures thereof, or, alternatively, a mixture of said organic solvent and water.

The compound of formula (I) [Olopatadine] is an amine and can form addition salts with organic or inorganic acids when it reacts with a stoichiometric amount of the suitable acid in water, in an organic solvent or in a mixture of both. Usually the preferred non-aqueous media are diisopropyl ether, ethyl acetate, ethanol, isopropanol or acetonitrile. The acid addition salts include mineral acid addition salts such as hydrochloride, hydrobromide, sulfate, nitrate and phosphate, and organic acid addition salts such as acetate, maleate, fumarate, lactate, citrate, oxalate, succinate, tartrate, malate, mandelate, methanesulfonate and p-toluenesulfonate. Said salts can be obtained by conventional methods by reacting the free amine with the acid in question. In a particular embodiment, said salt is a pharmaceutically acceptable salt, for example, hydrochloride. Said salt can be obtained by reacting the free amine with hydrochloric acid. Optionally, if desired, said addition salt can be transformed into the corresponding free amine by conventional methods, for example, varying the pH of a solution comprising said salt to obtain the free amine. In another particular embodiment, said salt is not a pharmaceutically acceptable salt, therefore it cannot be used in the preparation of pharmaceutical formulations; nevertheless, it can be interesting to produce said salts for the purposes of isolation and/or purification of the desired final product, e.g., Olopatadine or one of its pharmaceutically acceptable salts. Additionally, Olopatadine can form base addition salts and metallic salts. Base addition salts can be obtained reacting Olopatadine with a stoichiometric amount of the suitable base, normally, an organic base, in a suitable solvent (e.g., water, an organic solvent, or mixtures thereof). The base addition salts include addition salts of organic amines, such as triethylamine, morpholine, etc. Said salts can be obtained by conventional methods by reacting the free acid with the base in question. The metallic salts of Olopatadine can be obtained reacting Olopatadine with a suitable base; non-limiting, illustrative examples of metallic salts of Olopatadine include the sodium, potassium, magnesium, calcium, aluminium, zinc salts, etc.

The compound of formula (I) [Olopatadine] can be obtained in the form of free base or of salt. In both cases it is preferably obtained in crystalline form, both as free compounds and as solvates (for example, hydrates), both forms being included within the scope of the present invention. The solvation methods are generally known in the state of the art.

In a particular embodiment, said addition salt is a pharmaceutically acceptable salt, for example, hydrochloride. Said salt can be obtained by reacting the free amine present in the compound of formula (I) [Olopatadine] with hydrochloric acid using a suitable solvent, preferably acetone.

Obtaining the compound of formula (I) can be carried out starting from the compound of general formula (II) without having to be isolated; alternatively, said compound can be isolated and, if desired, purified, by conventional methods. Thus, in a particular embodiment, the compound of formula (I) is obtained from the compound of general formula (II) obtained directly by means of the process of the invention, without having to be isolated. In another alternative particular embodiment, the compound of formula (I) is obtained from the compound of general formula (II) obtained by means of the process of the invention, isolated and, optionally, purified.

In any case, the compound of formula (II) can be transformed into Olopatadine (I), or a solvate or salt thereof, through a process comprising subjecting said compound of formula (II) to hydrolysis to obtain said compound of formula (I) and, if desired, converting said compound of formula (I) into a salt or solvate thereof.

In another aspect, the invention relates to a process for obtaining (Z)-11-(3-dimethylaminopropylidene)-6,11-dihydrodibenz[b,e]oxepin-2-acetic acid isopropyl ester of formula (IIa)

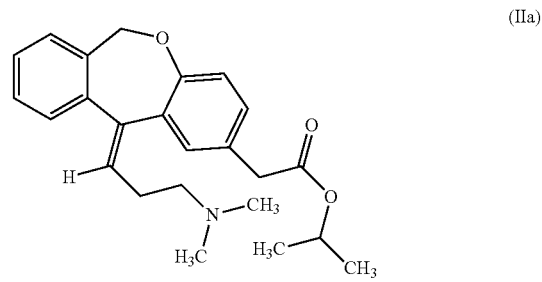 [SMILES: CC(C)OC(=O)Cc1ccc2c(c1)/C(=C\CCN(C)C)c1ccccc1CO2]

and salts thereof, comprising
a) reacting a compound of formula (III):

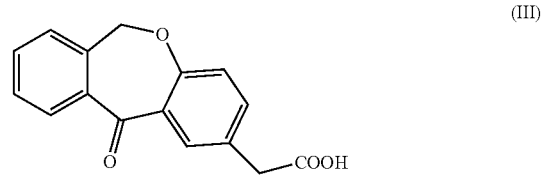 [SMILES: O=C(O)Cc1ccc2c(c1)C(=O)c1ccccc1CO2]

with isopropyl alcohol in an acid reaction medium comprising at least an organic solvent, for obtaining the compound of formula (IIIb)

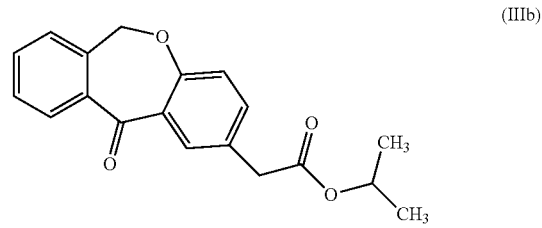 [SMILES: CC(C)OC(=O)Cc1ccc2c(c1)C(=O)c1ccccc1CO2]

b) subjecting said compound of formula (IIIb) to a Wittig reaction with a Wittig reagent selected from the group consisting of a (3-dimethyl-aminopropyl)-triphenylphosphonium halide and salts thereof, under Wittig reaction conditions, in the presence of a base, in a medium comprising an organic solvent, for obtaining said compound of formula (IIa); and, optionally
c) converting the compound of formula (IIa) into a salt thereof.

According to this process, the carboxylic group of Isoxepac (III) is protected by means of the formation of the isopropyl ester [step a)] by means of an esterification reaction comprising reacting Isoxepac with isopropanol in an acid reaction medium comprising one or more organic or inorganic acids, e.g., p-toluenesulfonic acid, benzenesulfonic acid, methanesulfonic acid, trifluoroacetic acid, etc.

Said reaction medium comprises isopropanol or a mixture comprising isopropanol and an organic solvent. Almost any organic solvent can be used together with the isopropanol; nevertheless, in a particular embodiment, said organic solvent is a solvent capable of carrying away the water which is being formed in the reaction, such as toluene, xylene etc.; in a preferred embodiment, the solvent used is only isopropanol which, by distillation, is also capable of carrying away the water which is being formed in the reaction and which, in addition, allows the isolation by filtration of the product formed which becomes insoluble upon lowering the temperature.

Then, in step b), the compound of formula (IIIb) is subjected to a Wittig reaction with a Wittig reagent selected from the group consisting of a (3-dimethylaminopropyl)-triphenylphosphonium halide and salts thereof, under Wittig reaction conditions, in the presence of a base, in a medium comprising an organic solvent, for obtaining said compound of formula (IIa). The reaction conditions are the same as those previously mentioned in relation to the process of the invention, therefore that mentioned in said process in relation to performing the Wittig reaction is applicable to this process.

Thus, in a particular embodiment, the Wittig reagent is a (3-dimethylaminopropyl)-triphenylphosphonium halide of general formula

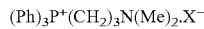

wherein Ph is phenyl and X is halogen, preferably, chlorine, bromine or iodine. In a specific embodiment, said (3-dimethylaminopropyl)-triphenylphosphonium halide is the (3-dimethylaminopropyl)-triphenylphosphonium bromide.

In another particular embodiment, said Wittig reagent is a salt of a (3-dimethylaminopropyl)-triphenylphosphonium halide of general formula

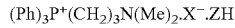

wherein Ph is phenyl and X and Z, independently from each other, represent a halogen, preferably, chlorine, bromine or iodine. In a specific embodiment, said salt of (3-dimethylaminopropyl)-triphenylphosphonium halide is (3-dimethylaminopropyl)-triphenylphosphonium bromide hydrobromide.

In a particular embodiment, the ratio between the Wittig reagent and the compound of formula (IIIb) is comprised between 1 and 2 equivalents of Wittig reagent per equivalent of compound of formula (IIIb).

Virtually any base capable of deprotonating the compound of formula (IIIb) can be used as a base, for example, a metal hydride, a metal alkoxide, a metal amide, an amide with great steric volume, etc., and mixtures thereof. In a particular embodiment, said base is selected from the group consisting of an alkali metal hydride, an alkaline-earth metal hydride, an alkali metal alkoxide, an alkaline-earth metal alkoxide, an alkali metal amide, an alkaline-earth metal amide, an amide with great steric volume, and mixtures thereof non-limiting, illustrative examples of said bases include lithium hydride, sodium hydride, potassium hydride, calcium hydride, sodium ethoxide, potassium ethoxide, sodium tert-butoxide, potassium tert-butoxide, sodium bis(trimethylsilyl)amide, lithium bis(trimethylsilyl)amide and mixtures thereof, preferably, sodium hydride, potassium ethoxide, potassium tert-butoxide and mixtures thereof. In a particular embodiment, the ratio between the base and the compound of formula (IIIb) is comprised between 1 and 2 equivalents of base per equivalent of compound of formula (IIIb).

Wittig reaction between the Wittig reagent and the compound of formula (IIIb), in the presence of a base, is carried out in a suitable organic solvent, for example, an aromatic solvent (e.g., toluene, xylene, etc.), a halogenated solvent (e.g., methylene chloride, etc.), an ether, for example, an aliphatic ether (e.g., diisopropyl ether, di-tert-butyl ether, etc.), a cyclic ether (e.g., tetrahydrofuran (THF), methyltetrahydrofuran (Me-THF)), dioxane (e.g., 1,3-dioxane, 14-dioxane and derivatives thereof), etc.), a polar aprotic solvent (e.g., dimethylformamide (DMF), dimethylacetamide (DMA), etc.), and mixtures thereof. In a particular embodiment, said solvent is selected from an aromatic solvent (e.g., toluene, xylene, etc.), an aliphatic ether (e.g., diisopropyl ether, etc.), a cyclic ether (e.g., THF, Me-THF, dioxane, etc.), and mixtures thereof, preferably, THF, toluene or mixtures thereof at a temperature comprised between 0° C. and the reflux temperature of the solvent used, for a time period equal or greater than 15 minutes, typically comprised between 30 minutes and 12 hours, usually, between 3 and 6 hours.

In a particular embodiment, the Wittig reaction is carried out using a metal alkoxide (e.g., potassium ethoxide, potassium tert-butoxide, etc.) as base in a reaction medium comprising THF as solvent.

In a preferred embodiment, the Wittig reaction is carried out using a metal alkoxide (e.g., potassium ethoxide, potassium tert-butoxide, etc.) as base in a reaction medium comprising toluene as solvent.

Additionally, it has been observed that when the base is a metal hydride (e.g., sodium hydride (NaH)), surprisingly, the Wittig reaction occurs very well when, in addition to the organic solvent, the medium comprises an organic polar aprotic cosolvent; in a particular embodiment, said polar aprotic cosolvent is selected from dimethylacetamide (DMA), dimethylformamide (DMF), N-methylpyrrolidone (NMP), N-methylmorpholine (NMM), and mixtures thereof, preferably, DMA, DMF and mixtures thereof, even more preferably, DMA. In a particular embodiment, the amount of said organic polar aprotic cosolvent present in the reaction medium is comprised between 2% and 50% by volume, preferably, between 5% and 20%, by volume of the cosolvent in relation to the amount of solvent present in the reaction medium.

Several combinations of bases and solvents have been tested and it has been observed that good results are obtained using a metal alkoxide (e.g., potassium ethoxide, potassium tert-butoxide, etc.) as base and THF or toluene as solvent; alternatively, good results were also obtained using a metal hydride (e.g., NaH, etc.) as base and a reaction medium comprising THF as solvent and DMA as organic polar aprotic cosolvent since, in these conditions, the Wittig reaction occurs very well, with a high yield, using a very small amount of Wittig reagent, typically, in the order of 1-1.6 equivalents of Wittig reagent per equivalent of compound of formula (IIIa), which facilitates both the processing and the production of Olopatadine and salts thereof at industrial level.

Finally, if desired, the compound of formula (IIa) can be converted into a salt by conventional methods as previously mentioned in relation to the compound of general formula (II).

The following examples illustrate the invention and must not be considered as limiting the scope thereof.

Example 1

Ethyl 6,11-dihydro-11-oxodibenz[b,e]oxepin-2-yl acetate 10 g (0.037 moles) of 6,11-dihydro-11-oxodibenz[b,e]oxepin-2-acetic acid were dissolved in 50 ml of ethanol (EtOH)

and 1 g (0.005 moles) of p-toluenesulfonic acid (p-TsOH) was added to this solution. The resulting solution was heated under reflux, distilling EtOH (10 ml) at atmospheric pressure which was put back immediately in the reaction medium. This operation was repeated several times for 90 minutes. After this time period, the reaction was cooled to 20-25° C. and 0.54 g (0.005 moles) of potassium acetate were added. Then, it was concentrated under reduced pressure until obtaining a residue on which 40 ml of $CH_2Cl_2$ and 10 ml of $H_2O$ were added. The mixture was stirred for 5 minutes and decanted, the organic phase being separated from the aqueous phase. The organic phase was concentrated under reduced pressure until obtaining a residue on which 20 ml of ethyl acetate (AcOEt) were added. The resulting suspension was stirred at room temperature (18-22° C.) for 30 minutes. After this time period the suspension was cooled at 0-5° C. for 30 minutes, and it was then filtered, washing the obtained solid with AcOEt at 0-5° C., which was dried in oven with air circulation at 50-55° C., thus obtaining 10.2 g (0.034 moles, 93%) of a white solid identified as the compound of the title, the spectroscopic properties of which are:

$^1$H-NMR (CDCl$_3$, 400 MHz), δ: 1.24 (t, 3H); 3.61 (s, 2H); 4.14 (q, 2H); 5.15 (m, 2H), 7.00 (d, 1H); 7.33 (d, 1H); 7.42 (m, 2H); 7.52 (m, 1H); 7.86 (d, 1H); 8.09 (d, 1H) ppm.

$^{13}$C-NMR (CDCl$_3$, 400 MHz), δ: 14.28; 40.33; 61.04; 73.68; 121.09; 125.20; 127.87; 128.02; 129.30; 129.54; 132.49; 132.82; 135.64; 136.41; 140.52; 160.50; 171.49; 190.88 ppm.

MS, M$^+$+1: 297.10.

Example 2

Isopropyl 6,11-dihydro-11-oxodibenz[b,e]oxepin-2-yl acetate 10 g (0.037 moles) of 6,11-dihydro-11-oxodibenz[b,e]oxepin-2-acetic acid were dissolved in 150 ml of isopropanol (iPrOH) and 2 g (0.01 moles) of p-toluenesulfonic acid (p-TsOH) were added to this solution. The resulting solution was heated under reflux, distilling 100 ml of iPrOH from the reaction medium. The reaction was cooled to 40-45° C. and 1 ml (0.007 ml) of Et$_3$N was added. Then, the reaction mixture was left to cool to 20-25° C. and stirring was maintained at this temperature for 30 minutes. Then, the suspension was left to cool to 5-10° C., it was filtered and the resulting product was washed with iPrOH. 11 g (0.035 moles, 96%) of a white solid identified as the compound of the title were obtained, the spectroscopic properties of which are:

$^1$H-NMR (CDCl$_3$, 400 MHz), δ: 1.21 (d, 6H); 3.59 (s, 2H); 4.12 (m, 1H); 5.11 (s, 2H), 6.97 (d, 1H); 7.29 (d, 1H); 7.38 (m, 2H); 7.47 (m, 1H); 7.84 (d, 1H); 8.08 (d, 1H) ppm.

$^{13}$C-NMR (CDCl$_3$, 400 MHz), δ: 21.78 (2); 40.22; 68.35; 73.55; 120.95; 125.10; 127.93; 129.18; 129.42; 132.34; 132.72; 135.55; 136.31; 140.39; 160.40; 170.90; 171.37; 190.71 ppm.

MS, M$^+$+1: 311.12

Example 3

Benzyl 6,11-dihydro-11-oxodibenz[b,e]oxepin-2-yl acetate 10 g (0.037 moles) of 6,11-dihydro-11-oxodibenz[b,e]oxepin-2-acetic acid were dissolved in 100 ml of toluene and 2 g (0.01 moles) of p-toluenesulfonic acid (p-TsOH) and 17.5 ml (0.169 moles) of benzyl alcohol were added to this solution. The reaction was equipped with a Dean-Stark, a mixture of water/toluene thus being distilled. The reaction was maintained until 0.7 ml of water were collected. The reaction was left to cool to 20-25° C., at which temperature 1.5 ml (0.011 moles) of Et$_3$N were added. The resulting solution was concentrated under reduced pressure until obtaining a residue which was dissolved in isopropanol (50 ml), giving rise to a suspension. The obtained suspension was stirred at 20-25° C. for 30 minutes, then being cooled at 0-5° C. Stirring was maintained at this temperature for 30 minutes. Then, the suspension was filtered and washed, obtaining 12.5 g (0.036 moles, 98%) of a white solid identified as the compound of the title, the spectroscopic properties of which are:

$^1$H-NMR (CDCl$_3$, 400 MHz), δ: 3.70 (s, 2H); 5.14 (m, 4H), 7.02 (d, 1H), 7.33 (m, 1H); 7.41-7.46 (m, 4H); 7.52 (m, 3H); 7.88 (m, 2H); 8.15 (d, 1H) ppm.

$^{13}$C-NMR (CDCl$_3$, 400 MHz), δ: 39.95; 66.56; 73.37; 120.88; 124.92; 127.48; 127.64; 128.04 (2); 128.10; 128.39 (2); 129.05; 129.25; 132.32; 132.58; 135.33; 135.53; 136.20; 140.60; 160.72; 171.48; 191.01.

MS, M$^+$+1: 358.12.

Example 4

(Z)-11-(3-Dimethylaminopropylidene)-6,11-dihydrodibenz[b,e]oxepin-2-acetic acid

Part A: (Z)-11-(3-dimethylaminopropylidene)-6,11-dihydrodibenz[b,e]oxepin-2-acetic acid ethyl ester 21.49 g (0.050 moles) of (3-dimethylaminopropyl)-triphenylphosphine bromide were suspended in 80 ml of tetrahydrofuran (THF) in a reaction flask under a N$_2$ stream. 1.86 g (0.046 moles) of 60% NaH were carefully added, maintaining the obtained suspension at 20-25° C. Then, 10 ml of dimethylacetamide were slowly added to the previous suspension. The resulting mixture was heated at 35-40° C. for 1 hour. At the end of this time period, 10 g (0.031 moles) of ethyl 6,11-dihydro-11-oxodibenz[b,e]oxepin-2-yl acetate dissolved in 30 ml of THF were added dropwise to the previous solution. The reaction mixture obtained was maintained at 35-40° C. for 2 hours. After this time period, the reaction mixture was left to cool to a temperature lower than 10° C., then adding 150 ml of water on the reaction mixture. The solvent was eliminated by means of distillation under reduced pressure until obtaining an aqueous residue on which 100 ml of toluene were added. Subsequently, the organic and aqueous phases were decanted and separated. The organic phase was washed with concentrated HCl (2×50 ml). Then, the organic and aqueous phases were decanted and separated. The obtained aqueous phases were pooled and 100 ml of toluene and 2×10 ml of a solution of 20% Na$_2$CO$_3$ were added to them. The organic and aqueous phases were decanted and separated and the organic phase was concentrated under reduced pressure until obtaining a residue which was used without purifying in Part B.

The obtained product can be identified, after being purified by means of silica gel column chromatography. The compound of the title is eluted with a dichloromethane/methanol/ammonia (95/5/1) mixture, the spectroscopic properties of which compound are:

$^1$H-NMR (CDCl$_3$, 400 MHz), δ: 1.24 (t, 3H), 2.80 (s, 6H), 2.89 (m, 2H), 3.20 (m, 2H), 3.51 (s, 2H), 4.11 (m, 2H), 5.15 (bs, 2H), 5.63 (t, 1H), 6.82 (d, 1H), 7.04 (m, 2H), 7.25 (m, 4H) ppm.

$^{13}$C-NMR (CDCl$_3$, 400 MHz), δ: 14.41; 25.03; 40.12; 43.14; 57.33; 61.16; 70.93; 120.34; 123.95; 125.44; 126.34;

126.63; 127.72; 128.27; 129.33; 130.85; 131.64; 133.66; 143.74; 144.12; 154.96; 163.34; 172.27 ppm.

MS, M$^+$+1: 366.06.

Part B: (Z)-11-(3-dimethylaminopropylidene)-6,11-dihydrodibenz[b,e]oxepin-2-acetic acid The compound (Z)-11-(3-dimethylaminopropylidene)-6,11-dihydrodibenz[b,e]oxepin-2-acetic acid ethyl ester (residue obtained in Part A) was dissolved in 100 ml of acetone in a reaction flask. 3.4 ml (0.040 moles) of HCl were added to this solution. The reaction was heated under reflux for 10 hours, in which time the reaction passed from being a solution to being a suspension. After this time, the reaction was cooled until reaching 20-25° C. The solid was filtered, washed and the resulting product was dried in an oven with air circulation at 50-55° C., obtaining 5.2 g (0.015 moles, 50%) of a white solid identified as (Z)-11-(3-dimethylaminopropylidene)-6,11-dihydrodibenz[b,e]oxepin-2-acetic acid, isolated as hydrochloride, the spectroscopic properties of which are the following:

$^1$H-NMR (DMSO, 400 MHz), δ: 2.69 (s, 6H); 2.77 (m, 2H); 3.24 (m, 2H); 3.56 (s, 2H); 5.15 (bs, 2H); 5.62 (t, 1H); 6.76 (d, 1H); 7.06 (m, 2H); 7.30 (m, 4H) ppm.

$^{13}$C-NMR (DMSO, 400 MHz), δ: 25.12; 40.13; 42.44 (2); 56.02; 70.26; 119.95; 123.43; 126.62; 127.64; 128.03; 128.47 (2); 129.85; 131.34; 132.57; 134.12; 141.63; 145.25; 154.52; 173.67 ppm.

MS, M$^+$+1: 338.17

Example 5

(Z)-11-(3-Dimethylaminopropylidene)-6,11-dihydrodibenz[b,e]oxepin-2-acetic acid

Part A: (Z)-11-(3-dimethylaminopropylidene)-6,11-dihydrodibenz[b,e]oxepin-2-acetic acid isopropyl ester The process described in Part A of Example 4 was repeated but using isopropyl 6,11-dihydro-11-oxodibenz[b,e]oxepin-2-yl acetate instead of ethyl 6,11-dihydro-11-oxodibenz[b,e]oxepin-2-yl acetate. The residue obtained was used without purifying in Part B.

The obtained product can be identified, after being purified by means of silica gel chromatography. To that end, the compound of the title identified as (Z)-11-(3-dimethylaminopropylidene)-6,11-dihydrodibenz[b,e]oxepin-2-acetic acid isopropyl ester is eluted with a heptane/ethyl acetate/triethylamine (20/10/0.5) mixture, the spectroscopic properties of which compound are:

$^1$H-NMR (DMSO, 400 MHz), δ: 1.13 (d, 6H); 2.06 (s, 6H); 2.34 (m, 2H); 2.46 (m, 2H); 3.50 (s, 2H); 4.85 (m, 1H); 5.15 (bs, 2H); 5.64 (t, 1H); 6.74 (d, 1H); 7.05 (m, 2H); 7.32 (m, 4H) ppm.

$^{13}$C-NMR (DMSO, 400 MHz), δ: 22.21; 28.13; 40.32; 45.65; 59.34; 68.11; 70.14; 119.86; 123.85; 126.43; 126.94; 128.14; 128.48; 129.86; 130.74; 131.94; 132.63; 134.14; 139.38; 146.05; 154.53; 171.42 ppm.

MS, M$^+$+1: 380.21

Part B: (Z)-11-(3-dimethylaminopropylidene)-6,11-dihydrodibenz[b,e]oxepin-2-acetic acid 6.6 g (0.02 moles, 67%) of a white solid identified as (Z)-11-(3-dimethylaminopropylidene)-6,11-dihydrodibenz[b,e]oxepin-2-acetic acid, isolated as hydrochloride, were obtained from the residue obtained in Part A and following the same process as in Part B of Example 4, the spectroscopic properties of which solid have been previously described in Example 4.

Example 6

(Z)-11-(3-Dimethylaminopropylidene)-6,11-dihydrodibenz[b,e]oxepin-2-acetic acid

Part A: (Z)-11-(3-dimethylaminopropylidene)-6,11-dihydrodibenz[b,e]oxepin-2-acetic acid benzyl ester The process described in Part A of Example 4 was repeated but using benzyl 6,11-dihydro-11-oxodibenz[b,e]oxepin-2-yl acetate instead of ethyl 6,11-dihydro-11-oxodibenz[b,e]oxepin-2-yl acetate. The residue obtained was used without purifying in Part B.

The obtained product can be identified, after being purified by means of silica gel chromatography. To that end, the compound of the title identified as (Z)-11-(3-dimethylaminopropylidene)-6,11-dihydrodibenz[b,e]oxepin-2-acetic acid benzyl ester is eluted with a heptane/ethyl acetate/triethylamine (50/10/1) mixture, the spectroscopic properties of which compound are:

$^1$H-NMR (CDCl$_3$, 400 MHz): δ 2.08 (m, 2H); 2.25 (s, 6H); 2.42 (m, 2H); 3.53 (s, 2H); 5.24 (s, 2H); 5.34 (m, 2H); 5.98 (t, 1H); 6.63 (m, 1H); 6.85 (m, 1H); 6.99 (s, 1H); 7.08 (m, 1H); 7.16 (m, 2H); 7.24 (d, 1H); 7.32-7.38 (m, 5H) ppm.

$^{13}$C-NMR (CDCl$_3$, 400 MHz): δ 24.28; 45.93 (2); 48.36; 68.41; 75.71; 113.28; 114.78; 115.33; 126.94; 127.08; 127.18 (2); 127.72; 127.82; 128.27; 128.82; 128.93; 129.06 (2); 135.21; 137.03; 140.10; 158.45; 171.24 ppm.

MS, M$^+$+1: 428.21

Part B: (Z)-11-(3-dimethylaminopropylidene)-6,11-dihydrodibenz[b,e]oxepin-2-acetic acid 12.8 g (0.03 moles, 61%) of a white solid identified as (Z)-11-(3-dimethylaminopropylidene)-6,11-dihydrodibenz[b,e]oxepin-2-acetic acid, isolated as hydrochloride, were obtained from the residue obtained in Part A and following the same process as in Part B of Example 4, the spectroscopic properties of which solid have been previously described in Example 4.

Example 7

6,11-Dihydro-11-oxodibenz[b,e]oxepin-2-acetic acid dimethylamide 8 g (0.029 moles) of 6,11-dihydro-11-oxodibenz[b,e]oxepin-2-acetic acid were dissolved in 30 ml of acetonitrile and 0.15 ml of DMF were added to this solution. 2.3 ml (0.032 moles) of thionyl chloride were added to the resulting solution at 20-25° C. Once the reaction had ended, the reaction mixture is slowly poured over an aqueous solution of 40% Me$_2$NH (14.4 g, 0.32 ml) cooled at 0-5° C. and stirring was maintained at this temperature for 30 minutes. Subsequently, the organic part was distilled under reduced pressure and 80 ml of methylene chloride were added. The phases were decanted, separating the organic phase. The solvent was distilled, obtaining an oil with the product of the title with a yield of 60%.

Example 8

(Z)-11-(3-Dimethylaminopropylidene)-6,11-dihydrodibenz[b,e]oxepin-2-acetic acid

The product of the title was obtained following the process described in the Example 6 but using 6,11-dihydro-11-oxodibenz[b,e]oxepin-2-acetic acid dimethylamide [Example 7] as the starting material.

Example 9

(Z)-11-(3-Dimethylaminopropylidene)-6,11-dihydrodibenz[b,e]oxepin-2-acetic acid 3.98 g (0.009 moles) of (3-dimethylaminopropyl)-triphenylphosphine bromide and 2.0 g (0.006 moles) of ethyl 6,11-dihydro-11-oxodibenz[b,e]oxepin-2-yl acetate were suspended in 10 ml of tetrahydrofuran (THF) in a reaction flask under a $N_2$ stream. 0.98 g (0.009 moles) of potassium tert-butoxide were carefully added maintaining the obtained suspension at 30-35° C. The resulting mixture was heated at 35-40° C. for 3 hours. After this time period, the reaction mixture was left to cool at a temperature lower than 10° C., then adding 50 ml of water to the reaction mixture. The solvent was eliminated by means of distillation under reduced pressure until obtaining an aqueous residue to which 50 ml of toluene were added. Subsequently, the organic and aqueous phases were decanted and separated. The organic phase was washed with concentrated HCl (2×20 ml). Then, the organic and aqueous phases were decanted and separated. The obtained aqueous phases were pooled and 40 ml of toluene and 2×5 ml of a solution of 20% $Na_2CO_3$ were added. The organic and aqueous phases were decanted and separated and the organic phase was concentrated under reduced pressure until a residue was obtained. Said residue, which was used without purifying, was subjected to a treatment similar to that described in Part B of Example 4.

0.88 g (0.003 moles) of the product of the title, isolated as hydrochloride, were obtained with a yield of 44%, the spectroscopic properties of which product have been previously described in Example 4.

Example 10

(Z)-11-(3-Dimethylaminopropylidene)-6,11-dihydrodibenz[b,e]oxepin-2-acetic acid 3.96 g (0.009 moles) of (3-dimethylaminopropyl)-triphenylphosphine bromide were suspended in 30 ml of tetrahydrofuran (THF) in a reaction flask under a $N_2$ stream. 0.73 g (0.009 moles) of potassium ethoxide (EtOK) were added maintaining the suspension at 20-25° C. The resulting mixture was heated at 50-60° C. for 1 hour.

At the end of this time period, 2.0 g (0.006 moles) of ethyl 6,11-dihydro-1'-oxodibenz[b,e]oxepin-2-yl acetate dissolved in 10 ml of THF were added dropwise to the previous solution. The obtained reaction mixture was maintained at 50-60° C. for 2 hours. After this time period, the reaction mixture was left to cool at a temperature lower than 10° C., then adding 50 ml of water to the reaction mixture. The solvent was eliminated by means of distillation under reduced pressure until obtaining an aqueous residue on which 50 ml of toluene were added. Subsequently, the organic and aqueous phases were decanted and separated. The organic phase was washed with concentrated HCl (2×20 ml). Then, the organic and aqueous phases were decanted and separated. The obtained aqueous phases were pooled and 40 ml of toluene and 2×5 ml of a solution of 20% $Na_2CO_3$ were added. The organic and aqueous phases were decanted and separated and the organic phase was concentrated under reduced pressure until a residue was obtained. Said residue, which was used without purifying, was subjected to a treatment similar to that described in Part B of Example 4.

0.62 g (0.002 moles) of the product of the title, isolated as hydrochloride, were obtained with a yield of 32%, the spectroscopic properties of which product have been previously described in Example 4.

Example 11

(Z)-11-(3-Dimethylaminopropylidene)-6,11-dihydrodibenz[b,e]oxepin-2-acetic acid 16.12 g (0.037 moles) of (3-dimethylaminopropyl)-triphenylphosphine bromide were suspended in 60 ml of tetrahydrofuran (THF) in a reaction flask under a $N_2$ stream. 1.51 g (0.035 moles) of 60% NaH were carefully added maintaining the obtained suspension at 20-25° C. The resulting mixture was heated at 35-40° C. for 1 hour. At the end of this time period, 7.4 g (0.023 moles) of ethyl 6,11-dihydro-1'-oxodibenz[b,e]oxepin-2-yl acetate dissolved in 22 ml of THF were added dropwise to the previous solution. The obtained reaction mixture was maintained at 35-40° C. for 2 hours. After this time period, the reaction mixture was left to cool at a temperature lower than 10° C., then adding 110 ml of water to the reaction mixture. The solvent was eliminated by means of distillation under reduced pressure until obtaining an aqueous residue to which 75 ml of toluene were added. Subsequently, the organic and aqueous phases were decanted and separated. The organic phase was washed with concentrated HCl (2×40 ml). Then, the organic and aqueous phases were decanted and separated. The obtained aqueous phases were pooled and 100 ml of toluene and 2×8 ml of a solution of 20% $Na_2CO_3$ were added. The organic and aqueous phases were decanted and separated and the organic phase was concentrated under reduced pressure until a residue was obtained. Said residue, which was used without purifying, was subjected to a treatment similar to that described in Part B of Example 4.

2.96 g (0.008 moles) of the product of the title, isolated as hydrochloride, were obtained with a yield of 41%, the spectroscopic properties of which product have been previously described in Example 4.

Example 12

(Z)-11-(3-Dimethylaminopropylidene)-6,11-dihydrodibenz[b,e]oxepin-2-acetic acid 9.02 g (0.020 moles) of (3-dimethylaminopropyl)-triphenylphosphine bromide were suspended in 30 ml of toluene in a reaction flask under a $N_2$ stream maintaining the temperature at 20-25° C. At this temperature, 2.19 g (0.020 moles) of potassium tertbutoxide were carefully added, keeping temperature below 35° C. 3.0 g (0.009 moles) of ethyl 6,11-dihydro-11-oxodibenz[b,e]oxepin-2-yl acetate dissolved in 9 ml of toluene were added during 1 hour, maintaining the temperature at 35-40° C.

The resulting mixture was heated at 35-40° C. for 3 hours. After this time, the reaction mixture was left to cool to a temperature lower than 10° C., then adding 15 ml of water followed by the addition of 16 ml of toluene on the reaction mixture. Subsequently, the organic and aqueous phases were decanted and separated. The organic phase was washed with concentrated HCl (2×20 ml). Then, the organic and aqueous phases were decanted and separated. The obtained aqueous phases were pooled and 30 ml of toluene and 2×5 ml of a 20% $Na_2CO_3$ solution were added to them. The organic and aqueous phases were decanted and separated and the organic phase was concentrated under reduced pressure, acetone (21 ml) and hydrochloric acid (1.5 ml) were added heating the mixture at reflux for 6 hours, the mixture was cooled down to 20-25° C. and the obtained solid was filtered.

The title compound was obtained, isolated as hydrochloride, 1.91 g (0.006 moles, 64% yield), the spectroscopic properties of which have been previously described in Example 4.

The invention claimed is:

1. A process for obtaining a compound of general formula (II)

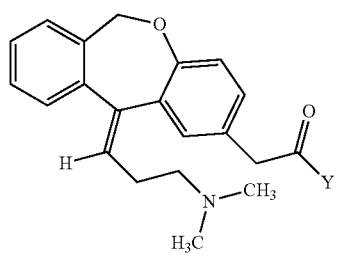

wherein
Y is
OR$_1$, wherein R$_1$ is $C_1$-$C_7$ alkyl, $C_3$-$C_7$ cycloalkyl, aryl, or heterocycle; or
NR$_2$R$_3$, wherein R$_2$ and R$_3$, independently from each other, are $C_1$-$C_7$ alkyl, aryl, or R$_2$ and R$_3$ together with the nitrogen atom to which they are bound form a heterocycle of 3 to 7 members,
or a solvate or a salt thereof,
comprising
a) reacting a compound of general formula (III)

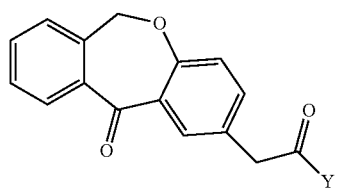

wherein Y has the previously mentioned meaning,
with a Wittig reagent selected from the group consisting of a (3-dimethylaminopropyl)triphenylphosphonium halide and salts thereof, under Wittig reaction conditions, in the presence of a base in a reaction medium comprising an organic solvent, for obtaining a compound of general formula (II); and
b) optionally, converting the compound of general formula (II) into a solvate or into a salt thereof.

2. Process according to claim 1, wherein said Wittig reagent is (3-dimethylaminopropyl)triphenylphosphonium bromide or a salt thereof.

3. Process according to claim 1, wherein the ratio between said Wittig reagent and said compound of general formula (III) is comprised between 1 and 2 equivalents of Wittig reagent per equivalent of compound of general formula (III).

4. Process according to claim 1, wherein said base is selected from the group consisting of a metal hydride, a metal alkoxide, a metal amide, an amide with great steric volume, and mixtures thereof.

5. Process according to claim 4, wherein said base is selected from the group consisting of lithium hydride, sodium hydride, potassium hydride, calcium hydride, sodium ethoxide, potassium ethoxide, sodium tert-butoxide, potassium tert-butoxide, sodium bis(trimethylsilyl)amide, potassium bis(trimethylsilyl)amide and mixtures thereof.

6. Process according to claim 1, wherein said organic solvent is selected from the group consisting of an aromatic solvent, a halogenated solvent, an ether, a polar aprotic solvent, and mixtures thereof.

7. Process according to claim 6, wherein said organic solvent is selected from the group consisting of toluene, xylene, methylene chloride, diisopropyl ether, di-tert-butyl ether, tetrahydrofuran (THF), methyl-tetrahydrofuran (Me-THF), dioxane, dimethylformamide (DMF), dimethylacetamide (DMA), and mixtures thereof.

8. Process according to claim 1, wherein said Wittig reaction is carried out using as base a metal alkoxide in a reaction medium comprising THF as solvent or using as base a metal alkoxide in a reaction medium comprising toluene as solvent.

9. Process according to claim 8, wherein said Wittig reaction is carried out using as base potassium tertbutoxide in a reaction medium comprising toluene as solvent.

10. Process according to claim 1, wherein said reaction medium further comprises an organic polar aprotic cosolvent.

11. Process according to claim 10, wherein said organic polar aprotic cosolvent is selected from the group consisting of dimethylacetamide (DMA), dimethylformamide (DMF), N-methylpyrrolidone (NMP), N-methylmorpholine (NMM), and mixtures thereof.

12. Process according to claim 1, wherein said base is sodium hydride and said medium comprises a solvent and an organic polar aprotic cosolvent.

13. Process according to claim 1, wherein said Wittig reaction is carried out using as base a metal hydride in a reaction medium comprising THF as solvent and DMA as organic polar aprotic cosolvent.

14. Process according to claim 1, wherein the obtained compound of formula (II) is transformed into Olopatadine, of formula (I)

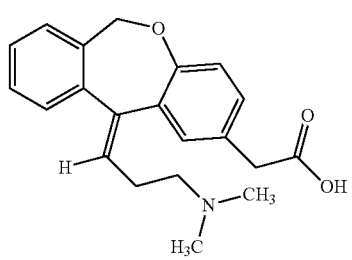

or a solvate or a salt thereof,
through a process comprising
a) subjecting to hydrolysis the compound of general formula (II)

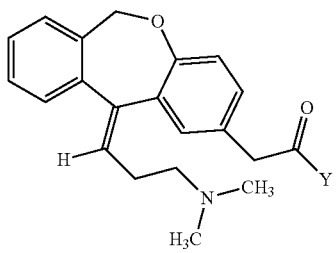

(II)

wherein

Y is

OR$_1$, wherein R$_1$ is C$_1$-C$_7$ alkyl, C$_3$-C$_7$ cycloalkyl, aryl, arylalkyl, or heterocycle; or NR$_2$R$_3$, wherein R$_2$ and R$_3$, independently from each other, are C$_1$-C$_7$ alkyl, aryl, or R$_2$ and R$_3$ together with the nitrogen atom to which they are bound form a heterocycle of 3 to 7 members, and, optionally, b) converting the obtained compound of formula (I) into a salt or solvate thereof.

15. A process for obtaining (Z)-11-(3-dimethylaminopropylidene)-6,11-dihydrodibenz[b,e]oxepin-2-acetic acid isopropyl ester of formula (IIa)

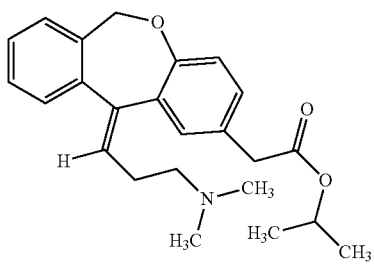

(IIa)

and salts thereof, comprising a) reacting a compound of formula (III):

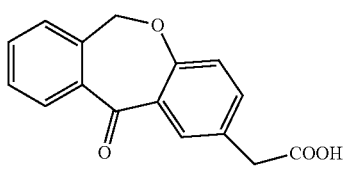

(III)

with isopropyl alcohol in an acid reaction medium comprising at least an organic solvent for obtaining the compound of formula (IIIb)

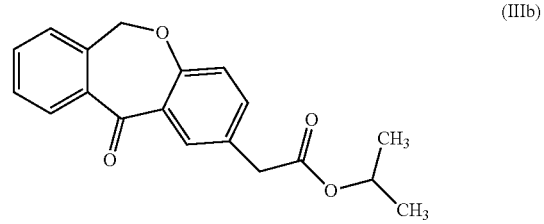 [SMILES: CC(C)OC(=O)Cc1ccc2c(c1)C(=O)c1ccccc1CO2]

(IIIb)

b) subjecting said compound of formula (IIIb) to a Wittig reaction with a Wittig reagent selected from the group consisting of a (3-dimethyl-aminopropyl)-triphenylphosphonium halide and salts thereof, under Wittig reaction conditions, in the presence of a base, in a medium comprising an organic solvent, for obtaining said compound of formula (IIa); and, optionally c) converting the compound of formula (IIa) into a salt thereof.

16. A compound selected from the group consisting of:

a) (11Z)-(3-dimethylaminopropylidene)-6,11-dihydrodibenz[b,e]oxepin-2-acetic acid isopropyl ester of formula (IIa)

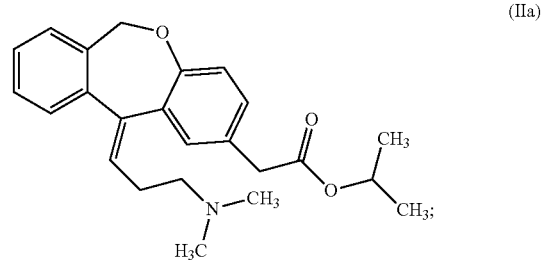 [SMILES: CC(C)OC(=O)Cc1ccc2c(c1)/C(=C\CCN(C)C)c1ccccc1CO2]

(IIa)

and b) (11Z)-(3-dimethylaminopropylidene)-6,11-dihydrodibenz[b,e]oxepin-2-acetic acid benzyl ester of formula (IIb)

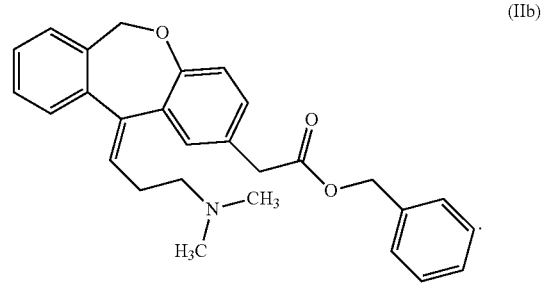 [SMILES: CN(C)CC/C=C1/c2ccccc2COc2ccc(CC(=O)OCc3ccccc3)cc21]

(IIb)

17. Process according to claim 1, wherein said Wittig reaction is carried out using as base a metal alkoxide in a reaction medium comprising THF as solvent.

18. Process according to claim 17, wherein said Wittig reaction is carried out using as base potassium tertbutoxide.

* * * * *

UNITED STATES PATENT AND TRADEMARK OFFICE
CERTIFICATE OF CORRECTION

PATENT NO. : 9,000,195 B2  
APPLICATION NO. : 13/054210  
DATED : April 7, 2015  
INVENTOR(S) : Silva Guisasola et al.

Page 1 of 1

It is certified that error appears in the above-identified patent and that said Letters Patent is hereby corrected as shown below:

Claims

Claim 14, Column 27, Line 18: change "arylalkyl, or heterocycle; or" to --or heterocycle; or--

Signed and Sealed this
Eighth Day of September, 2015

Michelle K. Lee
*Director of the United States Patent and Trademark Office*